United States Patent
Bugenske et al.

(10) Patent No.: US 9,724,440 B2
(45) Date of Patent: Aug. 8, 2017

(54) ENVIRONMENTAL CLEANING AND ANTIMICROBIAL LIGHTING COMPONENT AND FIXTURE

(71) Applicant: GE Lighting Solutions, LLC, East Cleveland, OH (US)

(72) Inventors: Matthew A. Bugenske, East Cleveland, OH (US); Sebastien Magnan, Lachine (CA); Francois Turgeon, Lachine (CA); Dengke Cai, E. Cleveland, OH (US); Jean-Francois Richard, Lachine (CA); Angela Wong, Lachine (CA)

(73) Assignee: GE LIGHTING SOLUTIONS, LLC, East Cleveland, OH (US)

( * ) Notice: Subject to any disclaimer, the term of this patent is extended or adjusted under 35 U.S.C. 154(b) by 0 days.

(21) Appl. No.: 14/081,805

(22) Filed: Nov. 15, 2013

(65) Prior Publication Data

US 2015/0151015 A1    Jun. 4, 2015

(51) Int. Cl.
*F21S 6/00*    (2006.01)
*A61L 2/10*    (2006.01)
(Continued)

(52) U.S. Cl.
CPC ............... *A61L 2/10* (2013.01); *A61L 2/088* (2013.01); *A61L 2/232* (2013.01); *A61L 9/18* (2013.01);
(Continued)

(58) Field of Classification Search
CPC ............ A01N 25/08; A61L 2/10; A61L 2/232
See application file for complete search history.

(56) References Cited

U.S. PATENT DOCUMENTS 6,387,844 B1 *  5/2002  Fujishima .............. B01J 21/10
                                                          252/373
6,764,655 B1    7/2004  Nishii et al.
(Continued)

FOREIGN PATENT DOCUMENTS

EP    1759034        10/2006
EP    2028417 A1    2/2009
(Continued)

OTHER PUBLICATIONS

PCT Search Report and Written Opinion issued in connection with corresponding PCT Application No. PCT/US2014/071148 dated Sep. 10, 2015.
(Continued)

*Primary Examiner* — Evan Dzierzynski
(74) *Attorney, Agent, or Firm* — GE Global Patent Operation; Peter T. DiMauro

(57) ABSTRACT

A system and method according to various embodiments combines three separate technologies to form a unique lighting system with enhanced antimicrobial properties and air cleaning capabilities. The combination of the three technologies also produces a lighting system that extends the required maintenance period for lighting fixtures. The first technology is based on anatase type $TiO_2$. The second and third technologies are based on the use of micro-sized surface structures to generate light scattering effects and, at the same time, reduce bacterial colonization and inhibit bacterial migration even during the absence of light or in dark environments.

16 Claims, 1 Drawing Sheet

Figure 1:
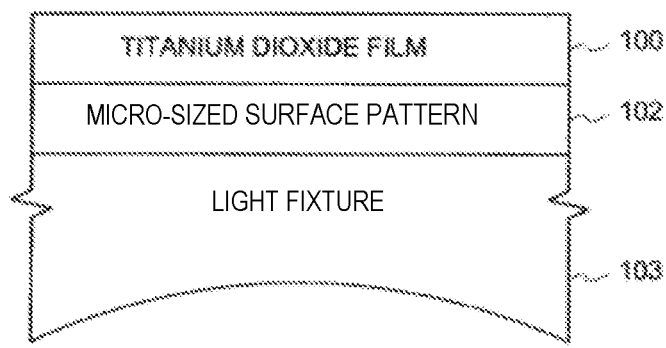

(51) Int. Cl.
*A61L 2/232* (2006.01)
*A61L 9/18* (2006.01)
*A61L 9/20* (2006.01)
*A61L 2/08* (2006.01)
*B29C 59/02* (2006.01)
*B29D 11/00* (2006.01)
*B29K 83/00* (2006.01)
*B29K 509/00* (2006.01)

(52) U.S. Cl.
CPC ............... *A61L 9/20* (2013.01); *A61L 9/205* (2013.01); *B29C 59/026* (2013.01); *B29D 11/00* (2013.01); *A61L 2209/12* (2013.01); *B29K 2083/00* (2013.01); *B29K 2509/00* (2013.01)

(56) References Cited

U.S. PATENT DOCUMENTS

| | | | |
|---|---|---|---|
| 7,327,074 | B2 | 2/2008 | Fujishima et al. |
| 7,667,407 | B2 | 2/2010 | Schlitt et al. |
| 8,080,490 | B2 | 12/2011 | Fechner et al. |
| 8,318,282 | B2 | 11/2012 | Ylitalo et al. |
| 8,512,322 | B1 | 8/2013 | Liu et al. |
| 2003/0035750 | A1 | 2/2003 | Neuberger |
| 2003/0108716 | A1 | 6/2003 | Nun et al. |
| 2003/0134086 | A1 | 7/2003 | Nun et al. |
| 2003/0147932 | A1 | 8/2003 | Nun et al. |
| 2004/0090429 | A1 | 5/2004 | Geaghan et al. |
| 2004/0228826 | A1 | 11/2004 | Yamamoto et al. |
| 2006/0086252 | A1 | 4/2006 | Huang |
| 2006/0210634 | A1 | 9/2006 | Moerck et al. |
| 2007/0000407 | A1 | 1/2007 | Leong |
| 2007/0237945 | A1 | 10/2007 | Ohrlander et al. |
| 2009/0041632 | A1 | 2/2009 | Day et al. |
| 2009/0045719 | A1* | 2/2009 | Schlitt .................. A61N 5/0614 313/486 |
| 2009/0103307 | A1 | 4/2009 | Shu |
| 2009/0197494 | A1* | 8/2009 | Chang et al. ................ 442/230 |
| 2009/0238811 | A1* | 9/2009 | McDaniel et al. ........... 424/94.2 |
| 2010/0126404 | A1 | 5/2010 | Brennan et al. |
| 2010/0143964 | A1* | 6/2010 | Mor et al. ........................ 435/34 |
| 2010/0272988 | A1* | 10/2010 | Wu .......................... C23C 14/14 428/328 |
| 2010/0279066 | A1 | 11/2010 | Bulliard et al. |
| 2011/0098724 | A1 | 4/2011 | Cichocki et al. |
| 2012/0058302 | A1 | 3/2012 | Eggenspieler et al. |
| 2013/0211310 | A1 | 8/2013 | Bommarito et al. |
| 2013/0273132 | A1 | 10/2013 | Eddy |

FOREIGN PATENT DOCUMENTS

| | | |
|---|---|---|
| EP | 2088131 | 8/2009 |
| WO | 2009056838 | 5/2009 |

OTHER PUBLICATIONS

Dengke Cai et al., U.S. Appl. No. 14/103,873, filed Dec. 12, 2013.
U.S. Non-Final Office Action issued in connection with related U.S. Appl. No. 14/103,873 dated Aug. 6, 2015.
Seery et al., "Silver Doped Titanium Dioxide Nanomaterials for Enhanced Visible Light Photocatalysis", Journal of Photochemistry and Photobiology A: Chemistry, pp. 258-263, 2007.
Pucher et al., "Nano-TiO2 Sols Immobilized on Porous Silica as New Efficient Photocatalyst", Applied Catalysis A: General, vol. No. 332, Issue No. 2, pp. 297-303, Nov. 1, 2007.
Giulio et al., "Photo-catalytic Coating of Polystyrene for Household Cooling Appliances with Self Cleaning Surfaces", Journal of Applied Electrochemistry, vol. No. 39, Issue No. 11, pp. 2265-2273, 2009.
Zhou et al., "Ag2O/TiO2 Nanobelts Heterostructure with Enhanced Ultraviolet and Visible Photocatalytic Activity", Applied Materials & Interfaces, vol. No. 2, Issue No. 8, pp. 2385-2392, 2010.
Winzenburg et al., "Efficient Photocatalysis in the Visible with TiO2/Phthalocyanine-Hybrid Particles", 3rd International Symposium on Ultra-High Performance Concrete and Nanotechnology for High Performance Construction Materials, pp. 177-184, 2012.
International Search Report and Written Opinion issued in connection with corresponding PCT Application No. PCT/US2014/065661 dated May 12, 2015.

\* cited by examiner

ENVIRONMENTAL CLEANING AND ANTIMICROBIAL LIGHTING COMPONENT AND FIXTURE

I. FIELD OF THE INVENTION

The present disclosure relates generally to the field of lighting fixtures. More particularly, the present disclosure relates to reducing bacterial growth and maintaining a sanitary environment, for example, in a healthcare facility.

II. BACKGROUND OF THE INVENTION

It is estimated that between 5% and 10% of patients admitted to hospitals acquire one or more healthcare-associated infections, which leads to more than a million people worldwide being affected by infections acquired in hospitals. Health-care associated infections are also an important problem in extended care facilities, including nursing homes and rehabilitations units. These health-care acquired infections are associated with nearly 100,000 deaths annually.

Patients infected with healthcare-associated microbes frequently contaminate items in their immediate vicinity with microbes that may remain viable on surfaces for days to weeks. Contaminated surfaces in healthcare facilities contribute to the spread of healthcare-associated microbes. In some instances, patients acquire microbes following direct contact with contaminated equipment or other surfaces. Contaminated surfaces can act as sources from which healthcare workers contaminate their hands. Healthcare workers can contaminate their hands by touching contaminated surfaces, and can transmit microbes if their hands are not cleansed appropriately.

Inadequate cleaning of rooms after discharging a patient with certain contagious diseases put subsequent patients admitted to the room at risk of acquiring the organism. Routine cleaning of patient rooms is often below the required standard. Therefore, improved cleaning and disinfection of the environment can reduce the risk of patients acquiring multi-drug resistant pathogens. Cleaning, disinfecting and sterilization save lives and improves patient outcomes. Providing patients with a safe environment of care requires appropriate cleaning and disinfection of medical equipment and environmental surfaces.

Thus, the use of ultraviolet (UV) lighting systems has become well known for disinfecting, sanitizing and sterilizing environments. Most commercially available lighting systems with antimicrobial functions combine various inorganic and organic based antimicrobial materials (AM) as additives blended into conventional materials, for example, polymethylmethacrylate (PMMA), polycarbonate (PC) and polyethylene (PE), etc. for lighting components such as diffusers to inhibit the growth of microbes on their outer surfaces. However, due to the intrinsic inhibition mechanism from the AM, a certain humidity level is required and the AM efficacy is reduced due to the accumulation of damaged microbes on the surface. Therefore, frequent cleaning is required every 3-4 days.

One commonly known cleaning technique is exposing titanium dioxide photocatalyst coating to UV light to provide a purifying coating process based on the science of photocatalysis. The principle of photocatalysis is to accelerate nature's cleaning and purifying process using light as energy. Photocatalyst coating is a "green" technology that can be applied on walls, ceiling, floor carpets, curtains, car interior, et seats, etc. and all kinds of surface to form an invisible film. The film can work all day to decompose all kinds or micro-organic matters, like bacteria, viruses, mold, formaldehyde, benzene, xylene, ammonia, VOCs, tough odors, etc.

With a constant amount of light provided, titanium dioxide photocatalyst an control and prevent growth of bacteria, germ, and mold. Any bacteria and germ can be killed and decomposed in environments such as hospitals, schools, public restrooms, restaurants, bars, club houses, theaters, daycare centers, convention centers, stadiums, and casinos.

Titanium dioxide is a safe and stable substance. Numerous applications have been developed from utilizing its photocatalytic reaction properties. Employing a light-catalyst or photocatalyst, titanium dioxide breaks down organic compounds and acts as both a sterilizer and deodorizer. Photocatalyst coating can transform any surface into self-cleaning, anti-bacterial, anti-fungal, and mold free surface. The hydrophilic property (or high water-affinity) of titanium dioxide, coupled with gravity, makes the coating self-cleaning.

Titanium dioxide photocatalyst coating has been proven to clean air and kill microbes by photocatalytic oxidation and the hydrophilic surface also enables easy cleaning. However, it has limited use in areas where at times there can be less UVA in the night or total absence of UVA during unused hours.

III. SUMMARY OF EMBODIMENTS OF INVENTION

Given the aforementioned deficiencies, a need exists for systems and methods that generate light scattering effects, simultaneously reduce bacterial colonization, and inhibit bacterial migration even during the absence of light or in dark environments. There also remains a need for an environmental cleaning and antimicrobial lighting method and device that reduces the need for frequent cleaning requirements.

In certain embodiments, the system and method combines three separate technologies to form a unique lighting system having enhanced antimicrobial properties and air cleaning capabilities. The combination of the three technologies also produces a lighting system that extends the required maintenance period for lighting fixtures. The first technology is based on anatase type $TiO_2$. The second and third technologies are based on the use of micro-sized surface pattern to generate light scattering effects and, at the same time, reduce bacterial colonization and inhibit bacterial migration even during the absence of light or in dark environments.

In certain embodiments, the system and method combines the photo-catalyzing effect provided from $TiO_x$, without using any antimicrobial additives. Physical inhibition of the microbe growth is provided by a micro-sized surface pattern, which also provides light scattering function. The combined techniques of the system and method improve various performance aspects of the lighting fixture, such as killing and inhibiting growth of anti-microbes, cleaning the surrounding air, and facilitating ease of cleaning maintenances.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

IV. BRIEF DESCRIPTION OF THE DRAWINGS

Figure 2:
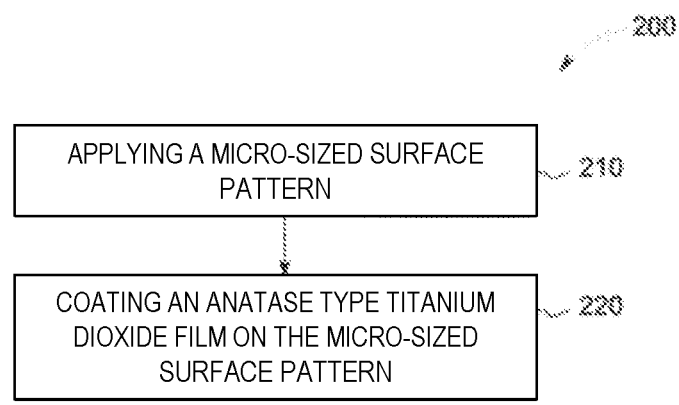

FIG. 1 is a partially sectional diagram for illustrating the configuration of an anatase titanium dioxide photocatalyst structure in accordance with the present teachings; and FIG. 2 is a flowchart of an exemplary method of practicing the present invention in accordance with the present teachings.

The present disclosure may take form in various components and arrangements of components, and in various process operations and arrangements of process operations. The present disclosure is illustrated in the accompanying drawings, throughout which, like reference numerals may indicate corresponding or similar parts in the various figures. The drawings are only for purposes of illustrating preferred embodiments and are not to be construed as limiting the disclosure. Given the following enabling description of the drawings, the novel aspects of the present disclosure should become evident to a person of ordinary skill in the art.

V. DETAILED DESCRIPTION OF VARIOUS EMBODIMENTS

The following detailed description is merely exemplary in nature and is not intended to limit the applications and uses disclosed herein. Further, there is no intention to be bound by any theory presented in the preceding background or summary or the following detailed description.

Throughout the application, description of various embodiments may use "comprising" language, however, it will be understood by one of skill in the art, that in some specific instances, an embodiment can alternatively be described using the language "consisting essentially of" or "consisting of."

For purposes of better understanding the present teachings and in no way limit the scope of the teachings, it will be clear to one of skill in the art that the use of the singular includes the plural unless specifically stated otherwise. Therefore, the terms "a," "an" and "at least one" are used interchangeably in this application.

Unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. In some instances, "about" can be understood to mean a given value.+−.5%. Therefore, for example, about 100 nm, could mean 95-105 nm. At the very least, each numerical parameter should at least be construed in light of the number of reported significant digits and by applying ordinary rounding techniques.

It should be understood that the terms titanium dioxide and $TiO_2$ as used throughout the disclosure are intended to mean anatase type crystal $TiO_2$ and also include other any other anatase crystal structure TiO containing hybrid materials Various embodiments provide a system and method that relates to antimicrobial function for lighting system and components. Various embodiments relates to a lighting method and system with antimicrobial properties and air cleaning capabilities supplied from titanium dioxide ($TiO^2$) and micro-sized surface pattern for the purpose of reducing bacterial growth and maintaining a sanitary environment, for example, in a healthcare facility.

In various embodiments, a system and method generates light scattering effects and simultaneously reduces bacterial colonization and inhibit bacterial migration even during the absence of light or in dark environments. Various embodiments provide a system and method for environmental cleaning and antimicrobial lighting that reduces the need for frequent cleaning requirements.

In various embodiments, the method combines three separate technologies to form a unique lighting system with enhanced antimicrobial properties and air cleaning functions. The combination of the three technologies also produces a lighting system that extends the required maintenance period for lighting fixtures.

The first technology is based on anatase type $TiO_2$. In some embodiments, the anatase type $TiO_2$ can be in a crystal form and approximately 10-60 nm thick. In lieu of the anatase type $TiO_2$, any doped metal or metal oxide that has been proven to clean air and kill microbes by photocatalytic oxidation and possess hydrophilic properties that enables a surface to be easily cleaned. For example, the doped metal or metal oxides can be selected from the group consisting of: Zn, Ag, Fe and Mn etc. All of these metals can be used, as the above list is not an elusive one, The second and third technologies are based on the use of a micro-sized surface pattern to generate light scattering effects and, at the same time, reduce bacterial colonization and inhibit bacterial migration even during the absence of light.

As shown in an example in FIG. 1, an anatase $TiO_2$ crystal thin film 100 having a thickness of approximately 10-100 nm or a metal doped with a $TiO_2$ crystal thin film is coated directly onto micro-sized surface pattern 102 on lighting fixture 103. This layer structure is designed for physically inhibiting the growth of microbes by decreasing bio-adhesion between microbes and substrate. The sub 100 nm thick $TiO_2$ coating will not change the shape of the micro-sized surface pattern, and will not affect its function of physically inhibiting microbe growth.

In various embodiments, the lighting system emits light having a wavelength in the range of approximately 250-450 nm with a light output of a minimum intensity of 0.1 uw/cm² on the outer surface of lighting fixture.

The micro-sized surface pattern (for example, having a feature size greater than 500 nm) can be transferred onto surfaces of optical components. Furthermore, components of lighting system, such as the diffuser and metal frames, can be encapsulated with the micro-sized surface pattern. The micro-sized surface pattern can be applied, for example, by roll-to-roll coating, etching, printing, transfer molding and thermal forming. Those skilled in the art would recognize a variety of techniques that may be used to encapsulate the lighting components. For example, there are several molding techniques available for encapsulating the components of the lighting system. The most widely used one is transfer molding.

However, other molding techniques such as injection molding, reaction-injection molding and compression molding can be used without departing from the scope of the invention. The micro-sized surface pattern and aspect ratio, which is the ratio of the width of the shape to its height, are optimized. This optimization not only meets optical and light distribution requirements, but also can achieve the highest antimicrobial (AM) efficacy to inhibit the growth in pathogens, such as *E-coli* and *Staphylococcus aureus* (*S. aureus*). This list of microbes is exemplary and nonlimiting.

After the application of the micro-sized surface pattern layer, another layer is applied. Anatase type $TiO_2$, metal doped anatase $TiO_2$ or anatase $TiO_x$ composed derivatives (like composite with SiOx, ZnO, and organic composition like —SiH etc.) is coated onto the micro-sized surface pattern with a thickness in the range of 10-1000 nm. In some embodiments, this layer can be a pure crystal thin film. In other embodiments this layer can be suspended with different binders. In between these two layers, in various embodiments, there can be another sub 100 nm organic or inorganic based buffer or protection layer, such as fluoropolymer, amorphous $TiO_2$, ZnO and $SiO_2$.

In some embodiments, anatase $TiO_x$ derivatives can be side attached with altering functional groups and with different polarities, which can vary the top $TiO_x$ coating surface from a hydrophilic surface to a hydrophobic surface, like CFx group combined anatase TiO hybrid. This provides a controllable surface energy for the top TiO coating, which extends the necessary cleaning period, because hydrophobic $TiO_x$ derivatives can be into hydrophilic under photon activation. In addition to that, like surface pattern hydrophobic surface has function to decrease bio-adhesion between microbes and substrate to further increase system AM efficacy and extend maintenance period. The hydrophobic surface can prevent damaged or decomposed microbes from adhering onto the micro-sized surface pattern and increases the continuous AM efficacy. Due to the high water affinity of the hydrophilic property, the hydrophilic surface can ease the task of cleaning, because the surface can be easily cleaned due to the improved water wetting.

FIG. 2 is a flowchart of an exemplary method 200 of practicing an embodiment of the present teachings. A method of providing a lighting system with enhanced antimicrobial properties, air cleaning capabilities, and the ability to extend the required maintenance period for lighting fixtures is described herein. In Step 210 of the exemplary method, a micro-sized surface pattern having, for example, a feature size greater than 500 nm is applied onto the surfaces of optical components and encapsulation components of the lighting system, such as the diffuser or metal frames, For example, the micro-sized surface pattern can be applied using techniques such as roll-to-roll coating, embossing, casting, transfer molding and thermal forming.

In Step 220, another layer is applied after the application of the micro-sized surface pattern layer in Step 210. In step 220, for example, an anatase type $TiO_2$, metal doped anatase $TiO_2$, or anatase $TiO_x$ composed derivatives (such as a composite with SiOx, ZnO, and organic composition like —SiH) are coated onto the micro-sized surface pattern with a thickness in the range of 10-1000 nm. In some embodiments, this layer can be a pure crystal thin film. In other embodiments this layer can be suspended with different binders. In between these two layers, in various embodiments, there can be another sub 100 nm organic or inorganic based buffer or protection layer, such as fluoropolymer, amorphous $TiO_2$, ZnO and $SiO_2$.

In general, a lighting system and method is provided that increases the AM efficacy of $TiO_2$ coating under dark environments. Micro surface structures with feature size >500 nm will inhibit bacterial growth and increase difficulties for microbes adhesion to the surfaces. These micro-structures do not require light to start antimicrobial function. $TiO_2$ requires light to function. However with the micro surface structures, this fixture will continue to have AM efficacy even under dark. The lighting system and method also decreases the necessary cleaning frequency and enables easy cleaning.

Without using any antimicrobial additives, the system and method combines the photo-catalyzing effect from anatase $TiO_x$ and enables physical inhibition of the microbe growth provided by the micro-sized surface pattern. The combined techniques of the system and method improve various performance aspects of the lighting fixture, such as killing and inhibiting growth of anti-microbes, cleaning air and facilitating easy maintenances.

For example, in conventional AM technologies, which provide air cleaning functions, very frequent maintenance (approximately every 3-4 days) is still required. In comparison to conventional $TiO_2$ coating technologies, less intensity of UVA is required to activate the anatase $TiO_x$ to kill microbes due to the inhibition of microbe growth from the micro-structure structure.

The use of less UVA minimizes the risk of degradation on various surrounding plastics materials. Furthermore, there is an advantage that no additional cost or a minimum cost is necessary for the application of the micro-sized surface pattern onto the diffuser for lighting fixtures currently installed in non-hospital facilities, because these lightings are oftentimes already installed within the facility.

The material and process cost for the $TiO_2$ is also very inexpensive due to the requirement of such a low dosage and the sub-100 nm thickness. From a cost prospective, the present invention is very competitive to current AM built-in and polymer based coating technologies. Moreover, this $TiO_2$ coating on microstructure technology improves fixture maintenance dramatically by reducing the cleaning frequencies and saves additional costs as well.

Alternative embodiments, examples, and modifications which would still be encompassed by the disclosure may be made by those skilled in the art, particularly in light of the foregoing teachings. Further, it should be understood that the terminology used to describe the disclosure is intended to be in the nature of words of description rather than of limitation.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

We claim:

1. A lighting system comprising:
    a light fixture configured to emit light including a region between a wavelength of 250 nm and 450 nm and comprising an outer surface having a minimum accumulated intensity of light of 0.1 $\mu W/cm^2$ for the region;
    a micro-sized surface pattern on surfaces of the lighting system configured to inhibit bacterial growth without requiring the use of light, and configured to scatter light; and
    a titanium oxide film formed on the micro-sized surface pattern.

2. The system according to claim 1, wherein the micro-sized surface pattern has a feature size greater than 500 nm.

3. The system according to claim 1, wherein the titanium oxide film comprises at least one of anatase type $TiO_2$ (titanium dioxide), metal doped anatase $TiO_2$ and anatase $TiO_x$ composed derivatives.

4. The system according to claim 1, wherein the thickness of the titanium oxide film is between 10-1000 nm.

5. The system according to claim 1, wherein the titanium oxide film comprises a crystal film.

6. The system according to claim 1, wherein the titanium oxide film is suspended with different binders.

7. The system according to claim 1, wherein the anatase $TiO_x$ composed derivatives are side attached with altering functional groups and with different polarities.

8. The system according to claim 1, wherein the lighting system further comprises an organic or inorganic buffer or a protection layer between the titanium oxide film and the micro-sized surface pattern.

9. A lighting system comprising:
a light fixture configured to emit light including a region between a wavelength of 250 nm and 450 nm, and comprising an outer surface having a minimum accumulated intensity of light of 0.1 $\mu W/cm^2$ for the region;
a micro-sized surface pattern on surfaces of the lighting system configured to inhibit bacterial growth without requiring the use of light, and configured to scatter light; and
a titanium oxide film formed on the micro-sized structure surface pattern, wherein the lighting system further comprises an organic or inorganic buffer or a protection layer between the titanium oxide film and the micro-sized surface pattern.

10. The system according to claim 9, wherein the micro-sized surface pattern has a feature size greater than 500 nm.

11. The system according to claim 9, wherein the titanium oxide film comprises at least one of anatase type $TiO_2$ (titanium dioxide), metal doped anatase $TiO_2$ and anatase $TiO_x$ composed derivatives.

12. The system according to claim 11, wherein the thickness of the titanium oxide film is between 10-1000 nm.

13. The system according to claim 11, wherein the titanium oxide film comprises a crystal film.

14. The system according to claim 11, wherein the anatase TiOx composed derivatives are attached with functional groups.

15. The system according to claim 9, wherein the thickness of the organic or inorganic buffer or the protection layer is less than 100 nm.

16. The system according to claim 9, wherein the organic or inorganic buffer or the protection layer comprises fluoropolymer, amorphous $TiO_2$, ZnO, and $SiO_2$.

* * * * *